United States Patent
Davis, III et al.

(10) Patent No.: US 11,096,577 B2
(45) Date of Patent: Aug. 24, 2021

(54) PROACTIVE PATIENT HEALTH CARE INFERENCE ENGINES AND SYSTEMS

(75) Inventors: Robert Thompson Davis, III, Marietta, GA (US); Jennifer M. Coleman, Cumming, GA (US); David Christopher Greig, Mableton, GA (US); Christopher Harley Davidson, Marietta, GA (US)

(73) Assignee: NXGN Management, LLC, Irvine, CA (US)

( * ) Notice: Subject to any disclaimer, the term of this patent is extended or adjusted under 35 U.S.C. 154(b) by 1113 days.

(21) Appl. No.: 13/288,323

(22) Filed: Nov. 3, 2011

(65) Prior Publication Data
US 2012/0143013 A1    Jun. 7, 2012

Related U.S. Application Data

(60) Provisional application No. 61/409,746, filed on Nov. 3, 2010.

(51) Int. Cl.
| | |
|---|---|
| *A61B 5/00* | (2006.01) |
| *G16H 50/20* | (2018.01) |
| *G16H 50/30* | (2018.01) |
| *G06F 19/00* | (2018.01) |

(52) U.S. Cl.
CPC ............ *A61B 5/0002* (2013.01); *G06F 19/00* (2013.01); *G16H 50/20* (2018.01); *G16H 50/30* (2018.01)

(58) Field of Classification Search
CPC .............................. G06Q 50/22; G06Q 50/24
See application file for complete search history.

(56) References Cited

U.S. PATENT DOCUMENTS

| | | | |
|---|---|---|---|
| 6,402,689 B1* | 6/2002 | Scarantino et al. | 600/300 |
| 7,558,687 B1* | 7/2009 | Bode | G05B 21/02 700/14 |
| 8,311,854 B1* | 11/2012 | Stanley et al. | 705/3 |
| 2004/0111296 A1 | 6/2004 | Rosenfeld | |
| 2004/0181433 A1 | 9/2004 | Blair | |
| 2004/0236189 A1* | 11/2004 | Hawthorne | G06F 19/3412 600/300 |
| 2005/0005202 A1 | 1/2005 | Burt | |
| 2005/0171818 A1 | 8/2005 | McLaughlin | |
| 2006/0235280 A1 | 10/2006 | Vonk | |
| 2007/0123755 A1 | 5/2007 | Rice | |
| 2007/0280431 A1 | 12/2007 | Alpsten et al. | |
| 2008/0077436 A1* | 3/2008 | Muradia | 705/2 |

(Continued)

FOREIGN PATENT DOCUMENTS

WO    2005114524    12/2005

OTHER PUBLICATIONS

International Search Report dated Feb. 26, 2013, for related PCT application No. PCT/US2012/063390.

*Primary Examiner* — Eliza A Lam
(74) *Attorney, Agent, or Firm* — Fish IP Law, LLP (57) ABSTRACT

Health care monitoring and alerting systems are presented. Contemplated systems include a rule repository storing rules for sending notifications to interested parties regarding a patient's wellness status. An inference engine correlates actual, possibly real-time, patient wellness information with rule sets. If a patient's wellness status satisfies triggering criteria of a rule sets, the inference engine instructs a communication engine to send a notification to interested parties according to the rules set.

24 Claims, 3 Drawing Sheets

(56) References Cited

U.S. PATENT DOCUMENTS

| | | |
|---|---|---|
| 2008/0091463 A1 | 4/2008 | Shakamuri |
| 2009/0043612 A1 | 2/2009 | Szela, Jr. et al. |
| 2009/0112114 A1* | 4/2009 | Ayyagari .................. A61B 5/08 600/529 |
| 2009/0216564 A1 | 8/2009 | Rosenfeld |

* cited by examiner

PROACTIVE PATIENT HEALTH CARE INFERENCE ENGINES AND SYSTEMS

This application claims the benefit of priority to U.S. Provisional Application No. 61/409,746 filed on Nov. 3, 2010. This and all other extrinsic materials discussed herein are incorporated by reference in their entirety. Where a definition or use of a term in an incorporated reference is inconsistent or contrary to the definition of that term provided herein, the definition of that term provided herein applies and the definition of that term in the reference does not apply.

FIELD OF THE INVENTION

The field of the invention is health care data management technologies.

BACKGROUND

Traditional approaches to patient visits rely on each patient's initiative to make appointments based on a yearly, or even a less frequent, exam schedule or perceived physical health. In so doing, it is difficult if not impossible to take a preventative approach to the patient's health. The possibility also exists of overlooking clinical symptoms which, if left untreated, could result in serious long-term degradation of patient health. A better system would fill the gap between physician care and patient initiative by proactively alerting physicians or patients when an appointment is deemed to be needed based on a periodic evaluation of each patient against predefined rule sets as a function of clinical and/or wellness measures Others have put forth some effort toward developing technology for sending appointment reminders to patients. For example, U.S. patent application publication to McLaughlin titled "Patient Communication Device and Method" filed Jan. 24, 2005, describes obtaining patient data from a healthcare facility. The McLaughlin system compiles sets of information, including appointment information, to create an appointment reminder sent to the patient. Similarly, U.S. patent application publication 2007/0280431 to Alpsten et al. titled "Messaging System" filed Jul. 3, 2007, also describes a system for sending messages to patients to remind them of appointments. Although these references are useful for reminding patients of a pre-scheduled appointment, they fail to recognize the need for a proactive scheduling system.

Still others have directed their efforts toward ensuring that a patient complies with a physician's instructions. For example, U.S. patent application publication 2004/0181433 to Blair titled "Patient Compliance and Follow-up Techniques" filed Mar. 11, 2004, describes a monitoring system that gathers post-visit information to determine a patient's compliance with instructions. In addition, U.S. patent application publication 2007/0123755 to Rice titled "System and Method for Repetitive Interval Clinical Evaluations" filed Sep. 25, 2006, describes a tool that allows a patient to record their own data. The tool can inform the patient if their parameters fall outside a control range. Even further examples include U.S. patent application 2008/0091463 to Shakamuri titled "Method for Online Health Management" filed Jun. 27, 2007; and U.S. patent application publication 2009/0043612 to Szela et al. titled "Electronic Health Management System" filed Aug. 7, 2008. These references make strides toward collecting data, but also fail to recognize the need for a proactive scheduling system.

What has yet to be appreciated is a health care ecosystem comprising many different, or even unaffiliated, health care data sources can leverage data across disparate data sources to determine if a patient should have an appointment with a health care provider.

Thus, there is still a need for health care management system capable of proactively contacting individuals.

SUMMARY OF THE INVENTION

The inventive subject matter provides apparatus, systems and methods in which a health care management system can analyze data from disparate data sources and determine if proactive steps should be taken with respect to a patient's health. Contemplated systems have health care data sources storing data related to patients. The data sources can be different from each other or unaffiliated and store various portions of a patient's data. In some embodiments, the patient's data can be stored as one or more well-defined wellness measures or can be converted to wellness measures. The system can further include a rule repository storing multiple rule sets comprising triggering criteria for an action to take place as a function of a patient's wellness measures. An inference engine obtains patient data from one or more of the data sources and correlates the patient's current wellness status with the rule sets to identify one or more event triggering rule sets having criteria at least partially satisfied by the patient's wellness measures. If triggering criteria of one or more identified event triggering rule sets are satisfied, the inference engine can take one or more actions associated with the identified rule set. One possible type of action includes causing a communication engine to send a notification to an individual associated with the patient's heath. For example, the notification could include appointment information for an automatically scheduled appointment created by the inference engine. The notification can be sent to the patient, a health care provider, or other entity.

Various objects, features, aspects and advantages of the inventive subject matter will become more apparent from the following detailed description of preferred embodiments, along with the accompanying drawing figures in which like numerals represent like components.

DETAILED DESCRIPTION

It should be noted that while the following description is drawn to a computer/server health care management system, various alternative configurations are also deemed suitable and may employ various computing devices including servers, interfaces, systems, databases, engines, controllers, or other types of computing devices operating individually or collectively. One should appreciate the computing devices comprise a processor configured to execute software instructions stored on a tangible, non-transitory computer readable storage medium (e.g., hard drive, solid state drive, RAM, flash, ROM, etc.). The software instructions preferably configure the computing device to provide the roles, responsibilities, or other functionality as discussed below with respect to the disclose apparatus. In especially preferred embodiments, the various servers, systems, databases, or interfaces exchange data using standardized protocols or algorithms, possibly based on HTTP, HTTPS, AES, public-private key exchanges, web service APIs, known financial transaction protocols, or other electronic information exchanging methods. Data exchanges preferably are conducted over a packet-switched network, the Internet, LAN, WAN, VPN, or other type of packet switched network.

One should appreciate that the disclosed techniques provide many advantageous technical effects including coordination communication among health care providers and a patient through electronic communication channels. The disclosed system can determine that proactive steps should be taken in an ecosystem where individuals lack complete visibility of a patient wellness status.

The following discussion provides many example embodiments of the inventive subject matter. Although each embodiment represents a single combination of inventive elements, the inventive subject matter is considered to include all possible combinations of the disclosed elements. Thus if one embodiment comprises elements A, B, and C, and a second embodiment comprises elements B and D, then the inventive subject matter is also considered to include other remaining combinations of A, B, C, or D, even if not explicitly disclosed.

As used herein, and unless the context dictates otherwise, the term "coupled to" is intended to include both direct coupling (in which two elements that are coupled to each other contact each other) and indirect coupling (in which at least one additional element is located between the two elements). Therefore, the terms "coupled to" and "coupled with" are used synonymously. Within a networking context, "coupled with" can also be construed to mean "communicatively coupled with".

Contemplated systems have a number of far-reaching, quantifiable benefits including the following:
  Improvement in the quality of patient care
  Improvement of the overall health of a practice's patients
  Increased involvement of patients in their health care
  Increased practice revenue due to increased rate of patient appointments
  Lowered healthcare costs due to the use of preventative healthcare measure
  Fulfillment of requirements of patient care as dictated by oversight entities By taking on some of the responsibility of initiating patient contact from the practice and implementing an automated, highly configurable process, the disclosed ecosystems improve both the frequency of patient visits and the reliability of patient contacts, resulting in improved quality of patient care and an increase in practice revenue. Patients can be automatically contacted using a variety of methods, prompting them to visit their provider for a visit based on the severity (e.g., urgency, priority, etc.) of the measure for which they are found to be out of compliance.

In such an ecosystem it is quite likely that any one data source (e.g., private practice, insurance company, the patient, etc.) would lack a complete view of available data. An inference engine can be constructed that has a view into all the data sources and can correlate a comprehensive view of the patient's data against event triggering rule sets, include rule sets that trigger scheduling an appointment as a preventative measure. Notifications can be sent to the patient, the provider, or other entity within the ecosystem as desired.

Figure 1:
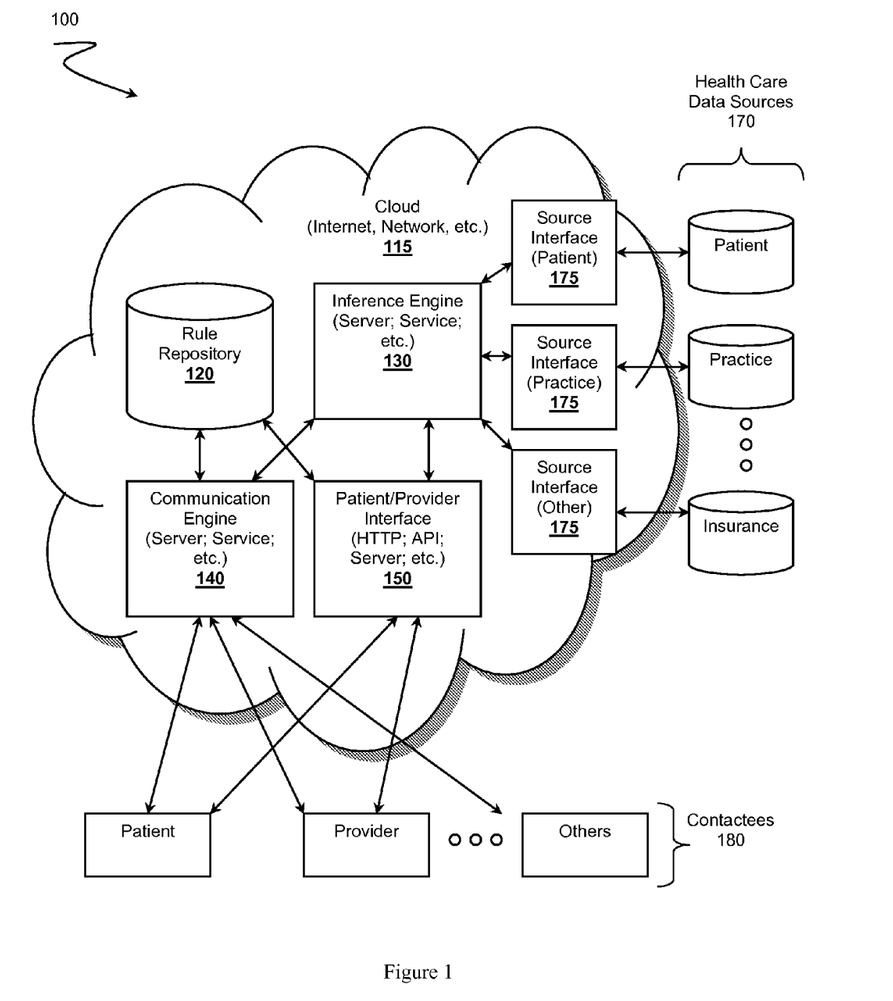
FIG. 1 is a schematic of a proactive health care data management ecosystem.

FIG. 1 presents an overview of health care data management ecosystem 100 configured to monitor patient data from multiple disparate health care data sources 170. When a wellness status of a patent sufficiently satisfies one or more rule sets stored in rule repository 120, inference engine 130 can cause communication engine 140 to send a notification to various contactees 180 according the rule sets. The notifications can be sent via one or more of patient/provider interface 150, possibly operating as an HTTP server, API, web service, physical device, cell phone, or other type of communication interface. Contactees 180 can include the patient, health care providers, pharmacies, insurance companies, family members, friends, remote computer systems, or other entities able or configured to receive the notification.

Patient health care data is contemplated to cover a broad spectrum of data types. In more preferred embodiments, the health care data comprises data obtained or acquired that relates directly to the patient. Direct health care data could reflect body temperature, heart rate, respiration rate, airway patency, gate, heading, images of the patient, audio data from the patient (e.g., voice patterns, body sounds, etc.) or other information obtained directly from a patient. The health care data can also include indirect data that tangentially relates to the patient, but does not represent a measure of the patient's body. Example of indirect health care data could include a physical location of the patient (e.g., GPS coordinates, building, room, etc.), weather conditions (e.g., barometer readings, pollen count, etc.), family history, medical history, prescriptions, security camera data, or other information that can pertain to a patient even if the patient is not involved with the data collection. Health care data is contemplated to comprise temporal aspects, possibly representing one or more of a point of time in the past, at a current time, in real-time, or at a predicted or forecasted time.

Data sources 170 represent one or more sources of patient relevant data where the data sources 170 can be distributed remotely over a network (e.g., the Internet, LAN, WAN, VPN, etc.) or even throughout cloud 115 as illustrated. Data sources 170 can comprise one or more contemplated computing systems or devices. In some embodiments, data sources 170 could include databases owned or operated by distinct entities housing patient data. For example, an insurance company or pharmacy could store patient data. In such embodiments, each of data sources 170 can have a locally installed agent configured to communicate with the various elements of ecosystem 100 where the agents, if required, can convert proprietary data formats or schemas into a common format understood by inference engine 130 or other components.

Data sources 170 can be configured to share their respective data. In embodiments where data sources 170 comprise multiple unaffiliated health care entities or practices, data sources 170 can participate in a data share agreement with respect to the patient. A patient can use provider/patient interface 150 to configure or at least acknowledge such an agreement.

Data sources 170 could also include sensor platforms configured to capture data related to the patient. Sensor platforms could include dedicated devices specifically adapted to capture sensor data and possibly transmit data to inference engine 130 via source interfaces 175. Example dedicated devices could include EKG, ECG, EMG, or TENS devices, body-attached sensors (e.g., perfusion, blood pressures, etc.), imaging devices (e.g., CT, MRI, CAT, or ultrasound devices), or other types of dedicated devices that acquire data about a patient. Even security cameras or surveillance equipment could represent a type of data source 170. One should also appreciated that sensor platforms could include general purpose devices that can be configured to acquire data about a patient. In more preferred embodiments, a sensor platform can include a smart phone or cellular phone possibly running an application where the application configures the phone to acquire ambient data about the patient's environment or about the patient.

Data source interfaces 175 represent computing infrastructure configured to exchange or acquire data from data sources 170. In the example show, each type of data source 170 could have a corresponding source interface 175, possibly located within cloud 115. For example, a patient source interface 175 might include a web service that communicatively couples with a patient's cell phone, possibly via HTTP, SMS, email, or other protocols. When in cloud 115, source interfaces 175 can comprise a suitably configured server that supports a desired communication protocol (e.g., TCP/IP, UDP/IP, HTTP, HTTPS, SSL, SMTP, cellular, etc.). Although each of source interface 175 are illustrated within cloud 115, it is also contemplated that the roles or responsibilities of source interface 175 could be local to data sources 170, possibly a locally resident application software or agent.

Data sources 170 can be distinct, unaffiliated entities (e.g., entities that have different owners) that participate, at least at some level, in a patient's life. Data sources 170 preferably include private practices, hospitals, insurance companies, pharmacies, or other health care related entities. Non-health care entities can also be data sources 170 and can include the patient, Google™ having patient information (e.g., a calendar, emails, search history, etc.), Yahoo!™, government entity, family members, or other non-health care entitles. Preferably data sources 170 are members of an authorized data share group associated with the patient. Data sources 170 can be authorized or validated before access services offered by ecosystem 100.

Data sources 170 do not necessarily have to store patient health care data, but could simply transmit the data to cloud 115 if desired. For example, a patient's cell phone could periodically send a sensor snap shot (e.g., location, position, orientation, acceleration, temperature, etc.) directly to cloud 115 for storage while the sensor snapshot might not be locally stored on the cell phone for longer than a de minimis amount of time to transmit the data.

Data sources 170 can also store health care data for longer periods of time or permanently according to any desired schema. As discussed previously each database associated with data sources 170 could include agents capable of securely interacting with the databases and elements within cloud 115. In some embodiments, the disclosed elements of ecosystem 100 can communicate among each other using a common intermediary health care protocol. The patient data can include raw data or processed data, where agents convert the health care data from one format to another in a secure fashion. Further, agents, or other elements in ecosystem can convert patient health care data into one or more wellness measures that can be considered a wellness profile of the patent. For example, the inference engine can collect raw data from the various data sources and convert the patient data into a priori defined wellness measures.

Wellness measures can conform to one or more standards. Example standards include Physician Quality Reporting Initiative (PQRI) or its derivatives, Take Care New York (TCNY), Doctor's Office Quality Information Technology (DOQ-IT), Bridges To Excellence (BTE), Chronic Kidney Disease (CKD), or other known standards or those yet to be defined. It is also contemplated that participants in the system, a health care provider for example, can define one or more wellness measures that apply to a patient or to a patient population.

One should appreciate that a wellness measure can be derived from one or more data sources 170. In some embodiments, a definition of a wellness measure depends on health care data from different data sources 170. For example, a definition of a wellness measure might require real-time data from a patient's cell phone, current prescriptions on file at a pharmacy, and a medical history on file at a doctor's office or EMR facility. In such a scenario, no single source 170 would likely have a complete picture. Thus, a wellness measure used to correlate with rule sets can be derived or obtained from at least two distinct, unaffiliated health care data sources 170. Example unaffiliated health care data sources 170 could include a practice database, a patient database, a government database, a subscribed web service, or a non-health care related data source.

Figure 2:
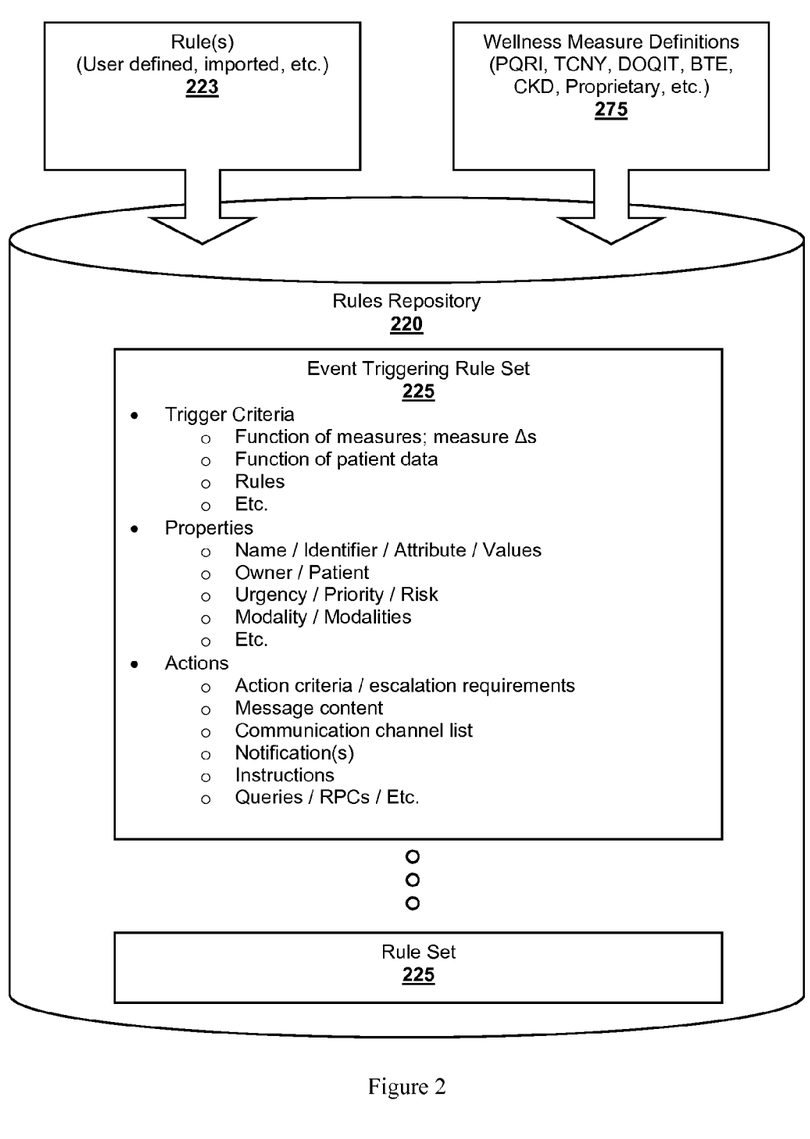
FIG. 2 is a schematic of a rule repository.

FIG. 2 provides additional information relating to rule repository 220. Rule repository 220 stores one or more event triggering rule sets 225. Each rule set 225 can include wellness measure criteria considered triggering criteria that should be satisfied, to at some degree, before an action takes place. In addition, each rule set 225 can include rules or instructions for taking an action that is considered to be proactive (i.e., initiated by the system as opposed to a provider or patient) or preventative. Thus, each rule set 225 represents criteria for triggering a proactive event, preferably sending a notification, when a patient's wellness status satisfies the criteria. Rule sets 225 can be based on wellness measure definitions 275 and possibly rules 223 obtained from a user. Rules 223 could include defined rules from known standards or defined from a user.

Rule sets 225 can take on many forms. In more preferred embodiments, rule sets 225 operate a function of one or more health care standards comprising wellness measure definitions 275. For example, a patient's wellness measures can be calculated or otherwise measured from one or more data sources, which provide access to processed or raw patient data, where the wellness measures are calculated according to the standards. Each wellness measure definition can include one or more attributes comprising values that outline or describe how the wellness measure relates to the patient, or to specific diseases, treatments, diagnosis, prognosis, or other health care related item. Each wellness measure definition 275 can comprise one or more properties, possibly functioning as a template that can be fleshed out to reflected specific aspects of event triggering rule set 225. For example, wellness measures in general can be compared against the standardized characteristics of a patient population considered at risk for a heart attack. Rule sets 225 can be custom designed to represent a proprietary wellness measure, possibly by participating entities (e.g., health care providers, insurance companies, subscribers to the system, etc.). Each rule set 225 can include one or more attributes, possibly including an urgency level, a priority level, or other attributes or properties. Example properties beyond urgency level or priority level could comprise a name, an identifier (e.g., GUID, UUID, etc.), an owner of who created rule set 225, modality of a resulting action (e.g., text, audio, video, still image, etc.), or other information.

One should note that rule set 225 can include more than one event triggering criteria set operating as a function of wellness measures or even changes in wellness measures (i.e., wellness measures deltas; Δ). For example, rule set might 225 represent a risk factor. As a patient's wellness state changes (i.e., the patient's wellness measures change), rule set 225 can be used to determine a current risk value to determine which actions should be taken. At low risk, the action might simply send an appointment to the patient. At high risk, the action might include contacting both the patient and the patient's primary health care providers or family by sending a high urgency, high priority message via one or more modalities (e.g., text, voices, image, etc.). Thus, rule set can 225 define rising risk factor that can be considered a leading indicator of possible problems with a patient's health.

Rule set 225 can include additional information beyond triggering criteria or properties. In addition, rule set 225 can include action related information outlining instructions through which a communication engine can engage with external entities, thus creating an action. When the triggering criteria have been satisfied with respect to wellness measures, the inference engine can use the action information to instruct the communication engine to send a notification. In some embodiments, the instructions relating to possible actions can be aggregated in the form of an XML serialized instruction set. The XML instruction set can configure the communication engine to construct and send out a desirable notification.

Consider a scenario where a patient is jogging. Ordinarily, heart rate data obtained from the patient during jogging might follow a regular pattern where the wellness measures indicate the patient is well within nominal values. In such conditions, the triggering criteria might require such values to send a low priority notification to the family physician notifying the physician that the patient did in fact exercise today. Still, during a jogging event, possibly defined in terms of patient data reflecting a time, place, rate of movement, heart rate, etc.; the patient's heart rate might increase outside of nominal bounds or fall near a threshold but still fall within nominal bounds. The triggering criteria could be triggered by a change in wellness measures as a function of time, which in turn sends a more urgent notification. The notification might include a scheduled appointment, messages to the patient, the family physician, or possible a cardiologist specialist.

A change in wellness measures, or a delta ($\Delta$), can be considered a quantifiable object. The inventive subject matter is considered to include tracking one or more wellness measures as a function of other variables, most preferably as a function of time. As a wellness measure changes, the change can be mapped to a delta object describing the change: a time of change, a magnitude of change, a context of a change, or other properties. Should the delta object satisfy triggering criteria, then the appropriate actions can take place accordingly to rules set 225.

Figure 3:
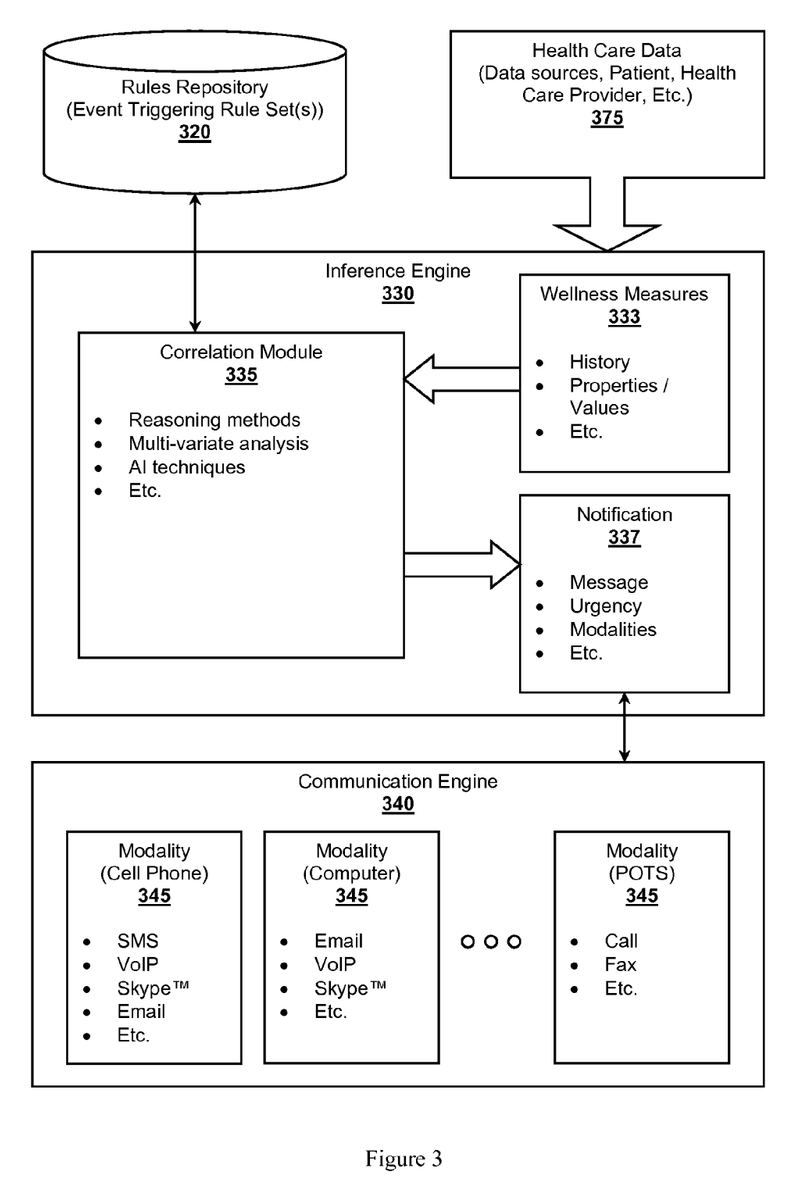
FIG. 3 is a schematic of an inference engine capable generating proactive notifications.

In FIG. 3, the ecosystem preferably includes one or more servers operating as inference engine 330 communicatively coupled with rules repository 320 and data sources providing health care data 375. Inference engine 330 can be configured with various algorithms to correlate a patient's wellness measures 333 with appropriate rule sets from rule repository 320. Preferred inference engines 330 include correlation module 335 configured to utilize one or more AI techniques to establish a correlation between wellness measures 333 derived from health care data 375 and triggering rule sets within rules repository 320. Such techniques can be applied to patient populations from a statistical perspective to determine which triggering rules sets would or could be most beneficial to a patient as a proactive or preventative action. In a more straight forward embodiment, correlations can also be determined by a simple function. For example, wellness measure 333 values can be used as an indexing scheme into rules repository 320 where application rule sets are indexed by corresponding attributes or properties of the wellness measure 333 values. Thus, inference engine 330 can use non-NULL wellness measures 333 or corresponding values as an index into rule repository 320 to reference rule sets that operate based on the same wellness measures. The correlation function utilized by correlation module 335 can also be more complex based on artificial intelligence techniques; binary decision trees, genetic algorithms, neural networks, fuzzy logic, reasoning algorithms, or other techniques to correlate a wellness state with a rule set. Example reasoning algorithms include using deductive logic, abductive logic, or inductive logic to select triggering rules sets. Using such types of logic to analyze or reason through how wellness measures might relate to rule sets allows for discovering non-obvious triggering rules sets that are, or might be beneficial to a patient. Thus, inference engine 330 can include a feedback loop to determine how best to inform interested parties of a patient's wellness status as a function of observed patient behavior in response to receiving notifications.

When inference engine 330 identifies or selects one or more rule sets, inference engine 330 can determine if an event should be triggered. Triggering an event mainly takes the form of automatically taking action according the instructions in the selected rule sets. Actions can cover a broad spectrum of capabilities. Examples include updating data, running a calculation, generating a report, change a sampling rate on a sensor, turn sensors on or off, scheduling events, or other type of actions. More preferably, inference engine 330 constructs notification 337 according to instructions within the one or more identify rule sets. Notification 337 can include one or more preferred, possibly ranked, modalities along with a message, urgency, priority, or other information necessary to convey information to remote contactees.

Inference engine 330 can also be configured to correlate an identified rule set with a health care provider. One should keep in mind that a rule set could be patient agnostic or represent a template. Once the correlation between the patient's wellness state and a rule set is established, inference engine 330 can use the information available (e.g., patient information, an actual patient's wellness measure, etc.) to determine which health care provider should be contacted. For example, the rule set might require contacting a cardiologist, but the rule set lacks specific cardiologist information. Inference engine 330 can determine that at least some cardio data for a patient was pulled from one or more cardiologists, thus the engine can infer that one of the specific cardiologists can be selected for notifications.

One action of particular note, as discussed above, includes sending notification 337 or alert to a participating entity within the ecosystem. For example, inference engine 330 can engage communications engine 340 to send notification 337 to the patient, provider, or other individual or entity. An especially preferred notification 337 includes sending a message relating to an automatically scheduled appointment representing a proactive or preventative step with respect to the patient's health care.

Communications engine 340 can utilize nearly any form of communication modality 345 as illustrated and can select a communication channel modality 345 based on the rule set (e.g., urgency, priority, attributes, etc.). Contemplated communication channel modalities 345 include email, SMS, NextGen Worklog™, NextMD™ or a patient portal, a Interactive Voice Response system (IVR; e.g., Televox™, PhoneTree™), Skype™, letters or postcards, personal phone calls, or even a personal visit to the patient's residence assuming the urgency or priority dictates such actions. In some embodiments, notifications 337 can be constructed based on the urgency or priority of the message as determined by the identified rule set triggering notification 337. The rule set could include communication rules for creating a cascading communication protocol (CCP) defining which communication channels should be attempted when a first channel fails. The CCP could be dictated by urgency or priority associated with the condition that trigger the event.

Contemplated health care management systems can also protect patient's data or privacy according to standards or regulations. The communications among the various elements of the system can be configured to comply with HIPPA requirements, for example. Security can be enforced through authentication or validation systems (e.g., RADIUS, Kerberos, certifications, etc.), encryptions (e.g., SSH, SSL, AES, etc.), or other known approaches.

The system can also include one or more user interfaces as represented by the patient/provider interface 150 in FIG. 1. The user interfaces can be leveraged by participating entities in the system to access the various system elements. For example, a provider would likely use a provider interface, assuming proper authentication, to define customized event triggering rule sets, configure preferences, adjust correlation algorithms, or other purposes. A patient could use a personalized patient interface to input patient data, configure preference, receiving notifications, or otherwise interface with the element of the system.

The disclosed system, including inference engine 330, can operate as a for-fee subscriber based service as hosted within one or more cloud severs, real or virtual. Furthermore, inference engine 330, or other elements of the system, can be built within a cloud-based computing platform (e.g., Amazon® EC2, Apple® iCloud, Google® cloud services, etc.) and accessed by subscribers.

Additional features can include the following:

Supporting Health Quality Measure (HQM) interoperability.

Maintaining measures as they are added or incorporated in the ecosystem across vendor lines.

A centralized repository version within the cloud for measure evaluation, communications engine and better tracking of transactions sent.

Support for contacting an Interactive Voice Response (IVR) system, including response routing.

Support for contacting a call center.

Support for enhanced reporting beyond patient data including accounting, human resources, communication sent, etc.

Support for measure sets by specialty, or other attribute.

Support for filtering communications based on attributes of patient, location, rule sets, provider, or other entity within the system.

Include appointment logic that can evaluate the type of appointment on a calendar as a function of attributes including the type of appointment, urgency, priority, or other attributes.

Support custom definition of measures by the provider and contact based on those measures.

Integrate communications sent as part of EHR legal record. Add features to EHR template or data grid.

Support for capturing responses for applicable contact methods and track trends.

Generate actionable items in EPM (e.g., create an appt, schedule a call from a nurse, etc.) based on patient responses.

Support for drill down capabilities on reporting. For example, one can drill down on charges to determine ROI.

Support for licensing (a) by the rendering provider or resource (e.g., for appointment reminders), (b) by contact methods, or (c) by wellness measure set.

Support for running one or more inference engines under BBP.

Integrate calendars (e.g., Outlook™, Yahoo!, Google! etc.) into communications for determining when appointments should be or incorporating appointments into calendars.

It should be apparent to those skilled in the art that many more modifications besides those already described are possible without departing from the inventive concepts herein. The inventive subject matter, therefore, is not to be restricted except in the spirit of the appended claims. Moreover, in interpreting both the specification and the claims, all terms should be interpreted in the broadest possible manner consistent with the context. In particular, the terms "comprises" and "comprising" should be interpreted as referring to elements, components, or steps in a non-exclusive manner, indicating that the referenced elements, components, or steps may be present, or utilized, or combined with other elements, components, or steps that are not expressly referenced. Where the specification claims refers to at least one of something selected from the group consisting of A, B, C . . . and N, the text should be interpreted as requiring only one element from the group, not A plus N, or B plus N, etc.

What is claimed is:

1. A health care monitoring and alerting system, the system comprising:
    a sensor platform comprising a plurality of sensor devices attached to a patient;
    a healthcare provider computing device associated with a healthcare provider;
    one or more remote health care data source interfaces communicatively coupled with the sensor platform over a network, the one or more health care data source interfaces programmed to access sensor data associated with the patient from the sensor platform, the sensor data comprises patient healthcare data;
    a rules repository comprising a plurality of event triggering rule sets;
    an inference engine comprising at least one computing device and communicatively coupled with the rule repository and at least one of the health care data source interfaces over a network, where the inference engine is programmed to:
        derive wellness measures for the patient from patient healthcare data,
        correlate the wellness measures of the patient with at least a first rule of the event triggering rule sets,
        automatically re-configure a setting of the sensor platform according to at least the first rule of the event triggering rule sets to activate a previously inactivated sensor of the plurality of sensors, and
        derive updated wellness measures for the patient from the previously inactivated sensor; and;
    a communication engine communicatively coupled with the healthcare provider computing device over a network and programmed to schedule an appointment with the healthcare provider when the patient's updated wellness measures satisfy the rule;

wherein the wellness measures are derived from patient healthcare data, and;

wherein the patient healthcare data comprises at least one of environmental data and physical characteristics data of the patient.

2. The system of claim 1, further comprising a provider interface communicatively coupled with the inference engine.

3. The system of claim 2, wherein the event triggering rule sets are provided by an authorized health care provider.

4. The system of claim 1, further comprising a patient interface communicatively coupled with at least one remote health care data source from the plurality of remote health care data sources.

5. The system of claim 4, wherein the remote health care data source is configured to store patient-submitted patient data.

6. The system of claim 1, wherein the wellness measures are also derived based on historic data of the patient obtained from at least two distinct, unaffiliated health care data sources.

7. The system of claim 1, wherein the wellness measures conform to an industry standard wellness measures.

8. The system of claim 7, wherein the industry standard wellness measures are selected from the list comprising: Physician Quality Reporting Initiative, Take Care New York, Doctor's Office Quality Information Technology, Bridges to Excellence, and Chronic Kidney Disease.

9. The system of claim 1, wherein the inference engine is further programmed to correlate the rule with a health care provider.

10. The system of claim 1, wherein the communication engine is further programmed to apply the rule to transmit a signal to a health care provider. .

11. The system of claim 1, wherein the communication engine is further programmed to apply the rule to send information about the scheduled appointment to the patient.

12. The system of claim 1, wherein the communication engine is programmed to apply the rule to select a communication channel to send the appointment information.

13. The system of claim 12, wherein the communication channel comprises a constructed cascading communication protocol based on the rule.

14. The system of claim 1, wherein the healthcare provider computing device is selected from a plurality of different healthcare provider computing devices according to the rule.

15. The system of claim 1, wherein the environmental data comprises at least one of: location data and weather condition data.

16. The system of claim 1, wherein the physical characteristics data comprises at least one of: body temperature, heart rate, blood pressure, respiration rate, airway patency, and audio data from the patient.

17. The system of claim 1, wherein the rule defines a rising risk factor.

18. The system of claim 1, wherein the rule defines an urgency level associated with the notification.

19. The system of claim 1, wherein the rule defines a priority level associated with the appointment.

20. The system of claim 1, wherein the inference engine comprises a cloud-based computing platform.

21. The system of claim 1, wherein the inference engine is also communicatively coupled with a plurality of remote health care data sources that include at least one of the following: a practice database, a patient database, a government database, a subscribed web service, and a non-health care related data source.

22. The system of claim 1, wherein the inference engine comprises a for-fee subscriber network-based service.

23. The system of claim 21, wherein each remote health care data source in the plurality of remote health care data sources is controlled and managed by a different entity.

24. The system of claim 1, wherein the communication engine is further programmed to change a sampling rate of at least one of the plurality of sensor devices.

* * * * *